(12) United States Patent
Wolf

(10) Patent No.: US 9,254,075 B2
(45) Date of Patent: Feb. 9, 2016

(54) LOCATION OF FRAGMENTS DURING LITHOTRIPSY

(71) Applicant: Gyrus ACMI, Inc., Southborough, MA (US)

(72) Inventor: Stuart Wolf, Yokneam (IL)

(73) Assignee: Gyrus ACMI, Inc., Southborough, MA (US)

( * ) Notice: Subject to any disclaimer, the term of this patent is extended or adjusted under 35 U.S.C. 154(b) by 80 days.

(21) Appl. No.: 14/269,150

(22) Filed: May 4, 2014

(65) Prior Publication Data

US 2015/0313444 A1 Nov. 5, 2015

(51) Int. Cl.
| | | |
|---|---|---|
| *A61B 1/04* | (2006.01) | |
| *A61B 1/00* | (2006.01) | |
| *A61B 1/018* | (2006.01) | |
| *A61B 18/26* | (2006.01) | |
| *A61B 18/00* | (2006.01) | |

(52) U.S. Cl.
CPC .......... *A61B 1/00009* (2013.01); *A61B 1/00006* (2013.01); *A61B 1/00045* (2013.01); *A61B 1/018* (2013.01); *A61B 18/26* (2013.01); *A61B 2018/00982* (2013.01); *A61B 2018/263* (2013.01)

(58) Field of Classification Search
CPC ........... A61B 1/00009; A61B 1/00006; A61B 2018/00982; A61B 2018/263; A61B 18/26
See application file for complete search history.

(56) References Cited

U.S. PATENT DOCUMENTS

| | | |
|---|---|---|
| 4,316,467 A | 2/1982 | Muckerheide |
| 4,669,483 A | 6/1987 | Hepp et al. |
| 4,682,594 A | 7/1987 | Mok |
| 4,763,652 A | 8/1988 | Brisson et al. |
| 4,887,605 A | 12/1989 | Angelsen et al. |
| 4,939,336 A | 7/1990 | Meyer et al. |
| 4,942,878 A | 7/1990 | Dory |
| 4,984,575 A * | 1/1991 | Uchiyama .......... A61B 17/2255 600/439 |
| 5,358,466 A | 10/1994 | Aida et al. |
| 5,473,136 A | 12/1995 | Engelhardt et al. |
| 5,531,739 A | 7/1996 | Trelles |
| 5,643,250 A | 7/1997 | O'Donnell |
| 5,697,885 A | 12/1997 | Konomura et al. |
| 5,749,830 A | 5/1998 | Kaneko et al. |

(Continued)

FOREIGN PATENT DOCUMENTS

| | | |
|---|---|---|
| CA | 2362332 A1 | 8/2000 |
| CN | 1515231 A | 7/2004 |

(Continued)

OTHER PUBLICATIONS

International Application # PCT/US14/58147 Search Report dated Jan. 29, 2015.

(Continued)

*Primary Examiner* — John P Leubecker
(74) *Attorney, Agent, or Firm* — D.Kligler IP Services Ltd.

(57) ABSTRACT

A medical apparatus, including a lithotripsic device configured to break a stone into one or more fragments in a body lumen and an endoscope which is configured to obtain a captured image in the body lumen. The medical apparatus further includes an image processor which is configured to process the captured image and create a processed image for display on a monitor, and which is also configured to process and display a track of a movement of at least one of the stone or the one or more fragments.

9 Claims, 9 Drawing Sheets

(56) References Cited

U.S. PATENT DOCUMENTS

| | | | |
|---|---|---|---|
| 6,375,651 | B2 | 4/2002 | Grasso et al. |
| 6,454,761 | B1 | 9/2002 | Freedman |
| 7,967,016 | B2 | 6/2011 | Anderson et al. |
| 8,006,702 | B2 | 8/2011 | Lin |
| 8,235,968 | B2 | 8/2012 | Tremaglio |
| 8,414,472 | B2 | 4/2013 | Hagelauer |
| 8,535,250 | B2 | 9/2013 | Owen et al. |
| 8,535,293 | B2 | 9/2013 | Faherty et al. |
| 8,607,634 | B2 | 12/2013 | Bailey et al. |
| 8,659,646 | B2 | 2/2014 | Adler et al. |
| 8,753,332 | B2 | 6/2014 | Bragagna et al. |
| 2002/0103477 | A1 | 8/2002 | Grasso, III et al. |
| 2002/0119116 | A1* | 8/2002 | Sahatjian ............... A61B 17/22 424/78.31 |
| 2003/0149352 | A1 | 8/2003 | Liang et al. |
| 2004/0242961 | A1 | 12/2004 | Bughici et al. |
| 2004/0243123 | A1 | 12/2004 | Grasso, III et al. |
| 2005/0131339 | A1 | 6/2005 | Makin et al. |
| 2006/0020269 | A1 | 1/2006 | Cheng |
| 2006/0184076 | A1 | 8/2006 | Gill et al. |
| 2007/0016113 | A1 | 1/2007 | Buchholtz et al. |
| 2007/0016114 | A1 | 1/2007 | Buchholtz et al. |
| 2007/0021754 | A1 | 1/2007 | Chernenko et al. |
| 2007/0260112 | A1 | 11/2007 | Rahmani |
| 2008/0226029 | A1 | 9/2008 | Weir et al. |
| 2009/0275832 | A1 | 11/2009 | Gelbart et al. |
| 2009/0275866 | A1 | 11/2009 | Gelbart et al. |
| 2010/0092054 | A1 | 4/2010 | Hensley et al. |
| 2010/0185187 | A1 | 7/2010 | Yamashita et al. |
| 2011/0034832 | A1 | 2/2011 | Cioanta et al. |
| 2011/0054363 | A1* | 3/2011 | Cain ................ A61B 17/225 601/4 |
| 2011/0074943 | A1* | 3/2011 | Modell ............ A61B 1/00009 348/77 |
| 2011/0082452 | A1 | 4/2011 | Melsky et al. |
| 2011/0257523 | A1 | 10/2011 | Hastings et al. |
| 2011/0257561 | A1 | 10/2011 | Gertner |
| 2011/0263967 | A1* | 10/2011 | Bailey ................ A61B 8/085 600/411 |
| 2012/0316396 | A1 | 12/2012 | Robertson |
| 2013/0072753 | A1 | 3/2013 | Zappia et al. |
| 2013/0102932 | A1 | 4/2013 | Cain et al. |
| 2013/0116561 | A1 | 5/2013 | Rothberg et al. |
| 2013/0211294 | A1 | 8/2013 | Bohris |
| 2014/0276101 | A1 | 9/2014 | Asselin et al. |
| 2014/0336497 | A1 | 11/2014 | Gertner |
| 2015/0055821 | A1* | 2/2015 | Fotland ............. G06K 9/00221 382/103 |
| 2015/0078615 | A1* | 3/2015 | Staples, II ............... G06T 7/204 382/103 |
| 2015/0133728 | A1* | 5/2015 | Finkman ............ A61B 17/2202 600/108 |
| 2015/0213616 | A1* | 7/2015 | Kappeler .................. G06T 7/20 348/92 |

FOREIGN PATENT DOCUMENTS

| | | |
|---|---|---|
| CN | 1647774 A | 8/2005 |
| CN | 1695565 A | 11/2005 |
| DE | 4038295 A1 | 6/1992 |
| DE | 102006060070 A1 | 2/2008 |
| DE | 102009042276 A1 | 4/2011 |
| DE | 102011109069 A1 | 1/2013 |
| EP | 0194856 A2 | 9/1986 |
| EP | 0329492 A2 | 8/1989 |
| EP | 1882454 A2 | 1/2008 |
| EP | 1513463 B1 | 5/2011 |
| JP | H02161937 A | 6/1990 |
| JP | 0576539 A | 3/1993 |
| JP | H0584253 A | 4/1993 |
| JP | 05228158 A | 9/1993 |
| JP | H05285159 A | 11/1993 |
| JP | H0686782 A | 3/1994 |
| JP | 06217986 A | 8/1994 |
| JP | 4982638 B2 | 7/2012 |
| WO | 9214415 A2 | 9/1992 |
| WO | 9406380 A1 | 3/1994 |
| WO | 2005037062 A2 | 4/2005 |
| WO | 2011133922 A2 | 10/2011 |
| WO | 2013145708 A1 | 10/2013 |
| WO | 2013154708 A1 | 10/2013 |

OTHER PUBLICATIONS

Elmed Lithotripsy Systems, Vibrolith Plus, Intracorporeal Ultrasonic Plus Pneumatic Lithotripter with Integrated Adjustable Suction Device, 4 pages, Dec. 3, 2008.

Medsolution—an operating division of Medical Tourism Inc., "Lithotripsy", 4 pages, 2008 http://www.medsolution.com/surgery_urogen-lithotripsy.asp.

Waingankar et al., "Guidewires and Angled Catheters", Springer Science+Business Media New York, pp. 127-136, 2013.

Orkisz et al., "Image Based Renal Stone Tracking to Improve Efficacy in Extracorporeal Lithotripsy", The Journal of Urology, vol. 160, Issue 4, pp. 1237-1240, Oct. 1998.

Finkman et al., U.S. Appl. No. 14/076,314, filed Nov. 11, 2013.

International Application # PCT/US2015/026572 Search Report dated Jun. 12, 2015.

International Application # PCT/US2015/026571 Search Report dated Jun. 16, 2015.

U.S. Appl. No. 14/076,314 Office Action dated Jul. 8, 2015.

U.S. Appl. No. 14/274,726 Office Action dated Sep. 2, 2015.

U.S. Appl. No. 14/076,314 Office Action dated Oct. 8, 2015.

* cited by examiner

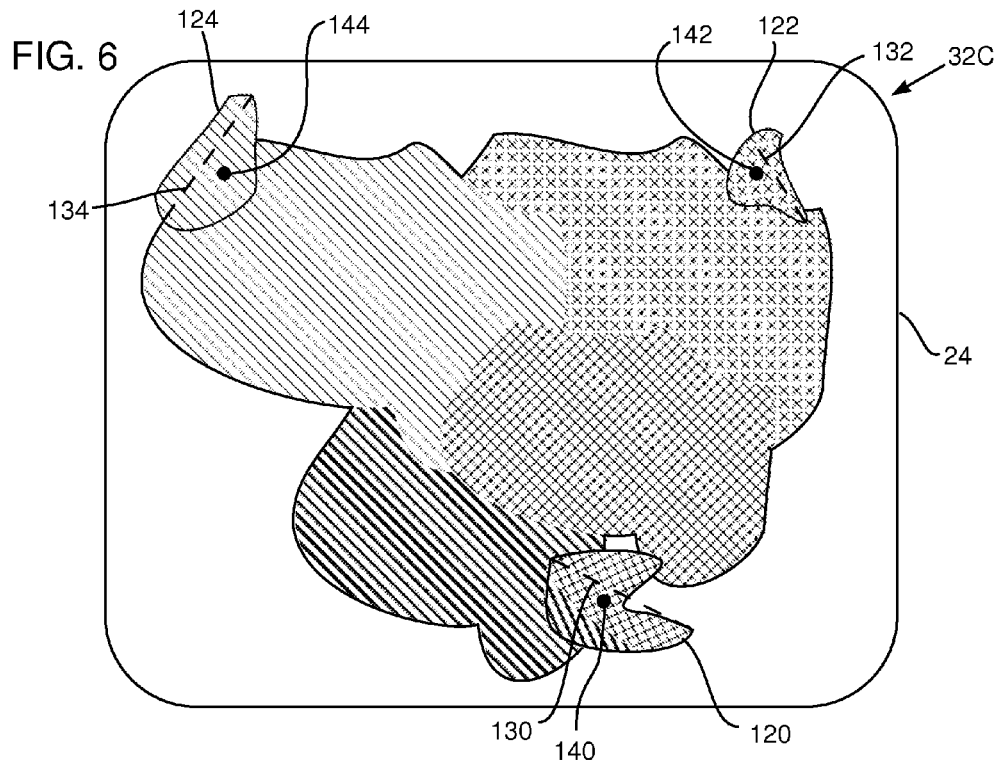
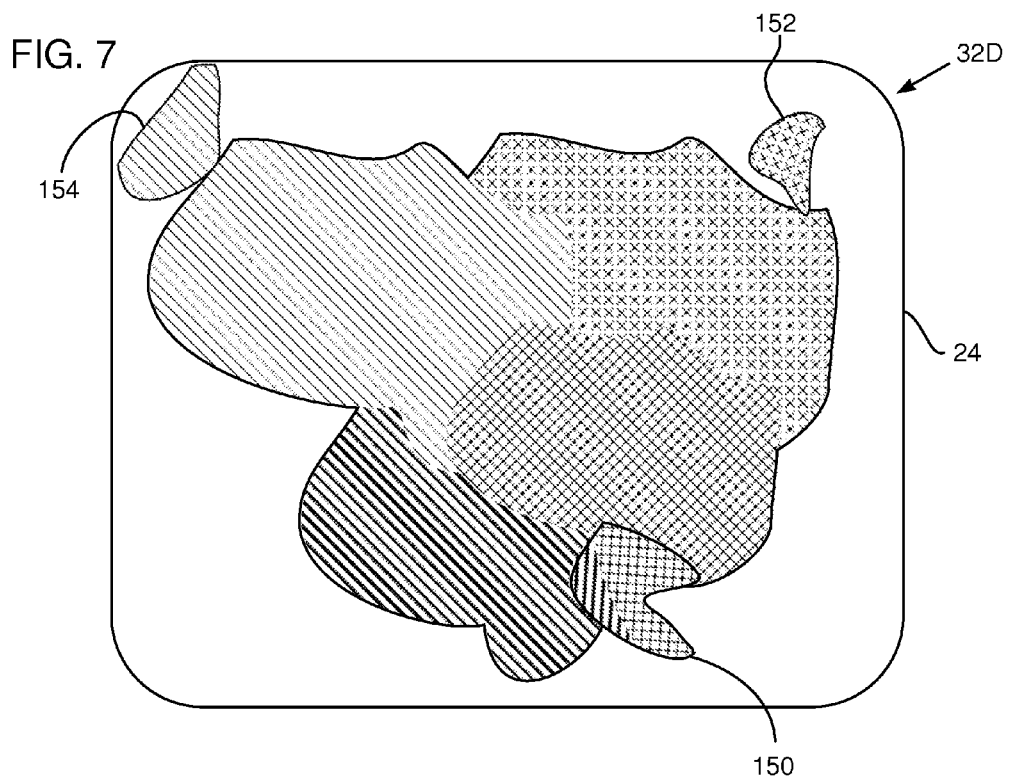

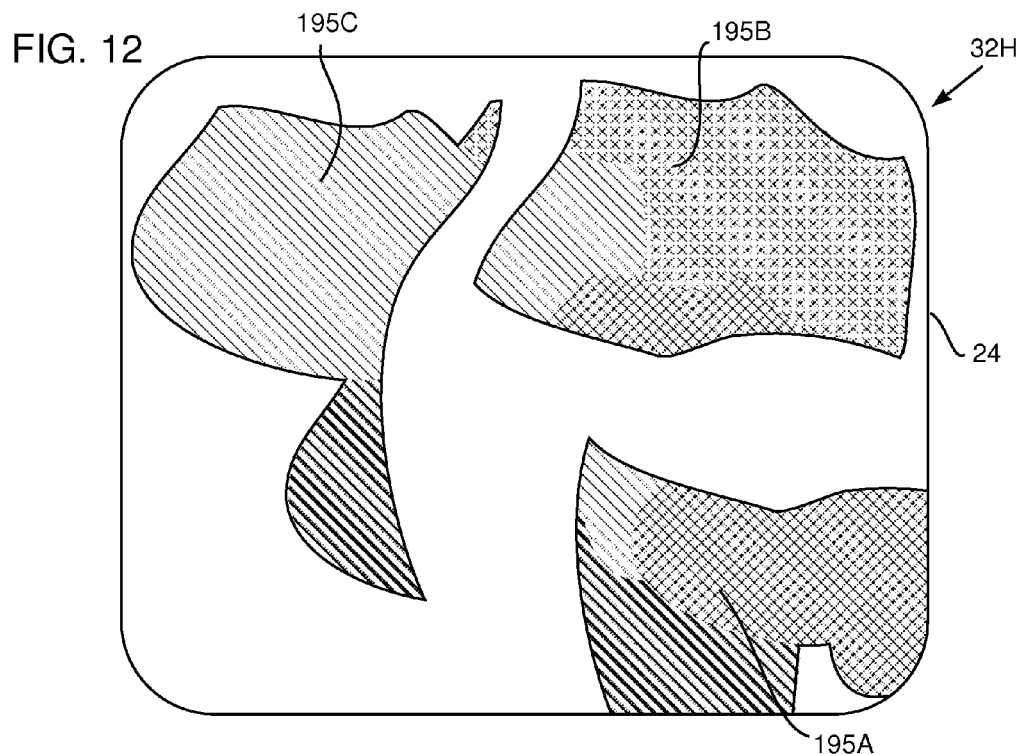
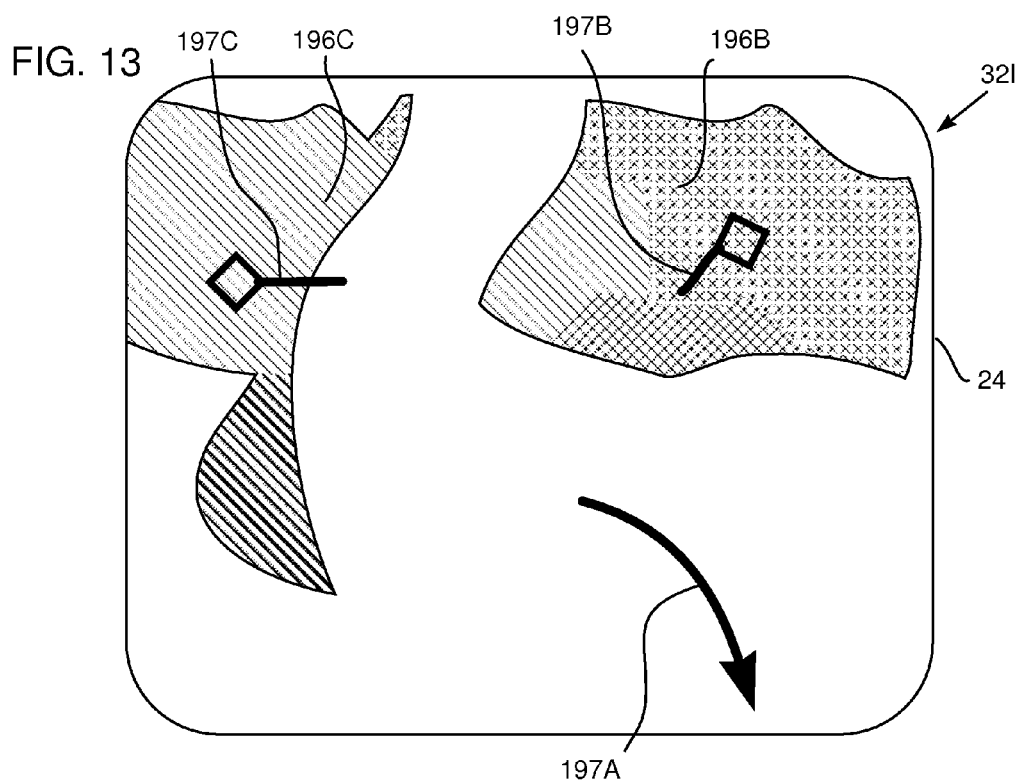

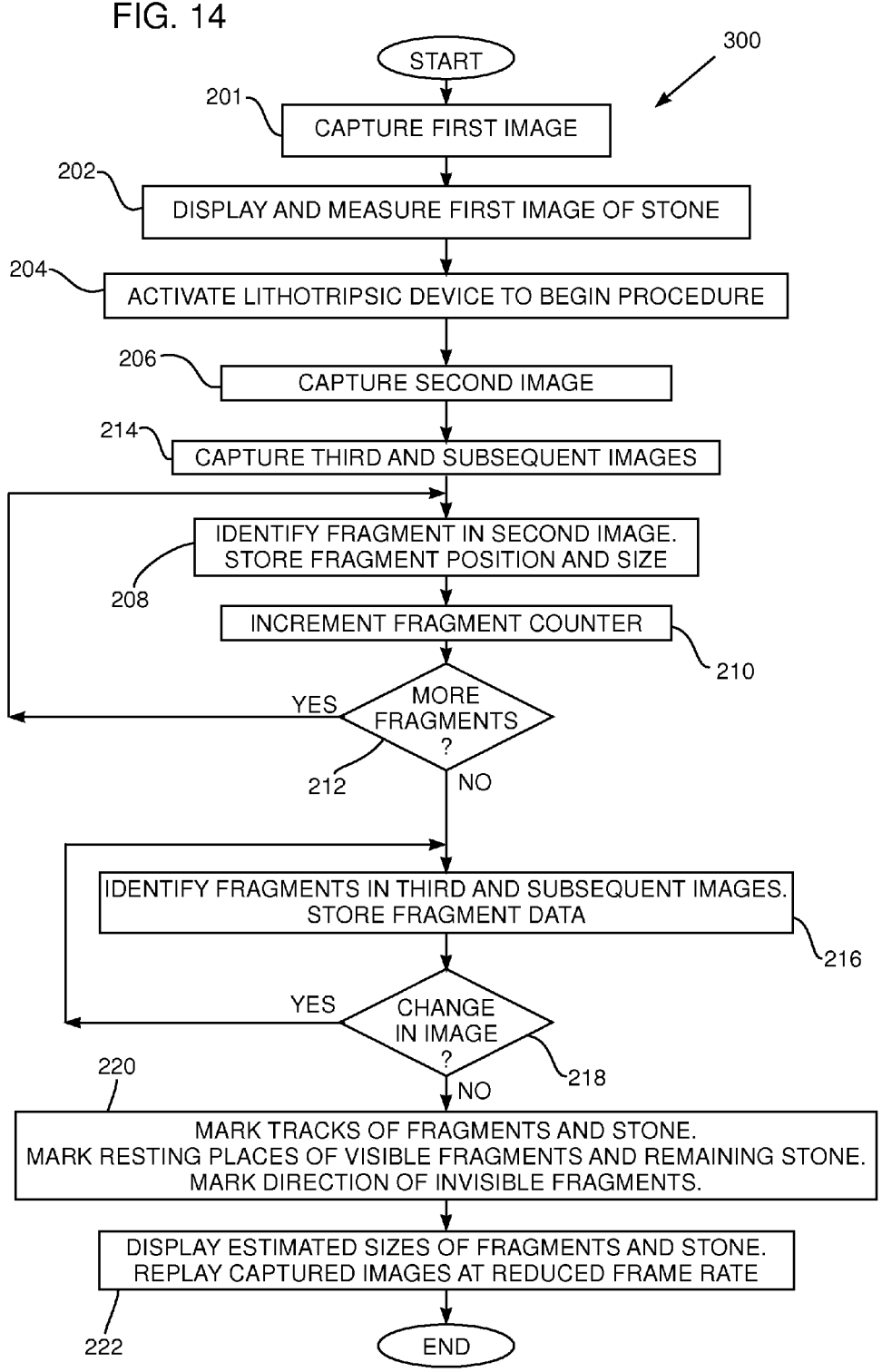

LOCATION OF FRAGMENTS DURING LITHOTRIPSY

FIELD OF THE INVENTION

The present invention relates generally to the medical procedure lithotripsy, and specifically to characterizing fragments produced during the procedure.

BACKGROUND OF THE INVENTION

A lithotripsy medical procedure consists of breaking a stone or other hardened mass into fragments, typically in a body lumen such as the bladder, so that the stone no longer affects operation of the lumen. The procedure inherently creates fragments of the stone being broken, and in a successful procedure the fragments are sufficiently small so that operation of the lumen is no longer affected.

US Patent Publication 2011/0054363, to Cain et al., whose disclosure is incorporated herein by reference, describes a device that delivers lithotripsy therapy to a patient so as to fractionate urinary stones in the patient. The device is claimed to be configured target and track urinary stones.

PCT Patent Publication 2011/133922, to Bailey et al., whose disclosure is incorporated herein by reference, describes a method for detecting stones by ultrasound, in which the ultrasound reflections from a stone are preferentially selected and accentuated relative to the ultrasound reflections from blood or tissue. The disclosure also describes displaying a stone as it is pushed in real time.

Japanese Patent Publication 05-076539, to Aida Satoshi et al., whose disclosure is incorporated herein by reference, describes a stone crushing device using a piezoelectric element. The device is claimed to exactly irradiate only a stone so as to decrease side effects.

US Patent Publication 2011/0074943, to Modell et al., whose disclosure is incorporated herein by reference, describes an imager configured to generate a plurality of frames at a frame frequency greater than an electromagnetic energy emission pulse frequency of a medical device. In the disclosure, an imaging system is claimed to be able to be used to locate a stone and to appropriately target treatment such that pulses are aimed at the place where the stone is located.

PCT Patent Publication 2013/154708, to Chia et al., whose disclosure is incorporated herein by reference, describes a surgical laser system for use in fragmenting of targeted kidney or bladder stones. The system has a laser probe which is optically coupled to a beam combiner and which is configured to output a combined laser pulse train.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides medical apparatus, consisting of:

a lithotripsic device configured to break a stone into one or more fragments in a body lumen;

an endoscope configured to obtain a captured image in the body lumen; and an image processor configured:

to process the captured image and create a processed image for display on a monitor, and to process and display a track of a movement of at least one of the stone or the one or more fragments.

Typically the lithotripsic device includes a laser configured to break the stone.

In a disclosed embodiment the processed image includes an image of a final location of the given fragment, and the image processor is configured to provide an indication of the final location on the processed image.

Typically, when a final location of the at least one of the stone or the one or more fragments is outside a field of view of the endoscope, the image processor is configured to provide an indication of a direction of the final location.

In a further disclosed embodiment the image processor is configured to measure a dimension of the stone, and a corresponding dimension of the one or more fragments, and to provide a comparison of the corresponding dimension to the dimension.

In a yet further disclosed embodiment the image processor is configured to evaluate a cardinality of the fragments.

In an alternative embodiment the image processor is configured to provide a comparison of a total size of the fragments to a size of the stone.

In a further alternative embodiment the image processor is configured to control a frame rate at which the endoscope obtains the captured image, and to increase the frame rate at least during activation of the lithotripsic device. Typically the image processor is configured to display the captured image at a lower frame rate than the increased frame rate on the monitor.

In a yet further alternative embodiment a direction of view of the endoscope is controlled by the image processor, and the image processor is configured to determine a location of one of the one or more fragments from the captured image, and to change the direction of view of the endoscope in response to the location so as to track the one of the one or more fragments.

There is further provided, according to an embodiment of the present invention a method, including:

providing a lithotripsic device configured to break a stone into one or more fragments in a body lumen;

configuring an endoscope to obtain a captured image in the body lumen;

processing the captured image and creating a processed image for display on a monitor; and processing and displaying a track of a movement of at least one of the stone or the one or more fragments.

The present invention will be more fully understood from the following detailed description of the embodiments thereof, taken together with the drawings in which:

BRIEF DESCRIPTION OF THE DRAWINGS

FIGS. 4-13 are schematic diagrams of images presented on a monitor, illustrating the steps of the flowchart, according to embodiments of the present invention; and FIG. 14 is a flowchart of steps performed by a processor in operating the system of FIG. 1, according to an alternative embodiment of the present invention.

DETAILED DESCRIPTION OF EMBODIMENTS

Overview

In performing a lithotripsy procedure it is useful to be able to track and characterize the fragments, so as to provide an operator of the procedure with information regarding the fragments. For example, the operator may decide that a particular fragment is too large, so that after breaking the stone the operator may decide to perform lithotripsy on the fragment of the stone. An embodiment of the present invention provides apparatus that enables an operator performing a lithotripsy procedure to track movements of fragments generated in the procedure, as well as to track any stone remaining after the fragments have been created. For clarity, in the following description of the apparatus the body lumen comprising the stone to be broken is assumed to be the bladder.

The apparatus comprises a lithotripsic device, typically a high-power laser generating a beam at a non-visible wavelength suitable for breaking a stone. The apparatus also comprises an endoscope, and in a disclosed embodiment the endoscope has a working channel within which a fiber optic is configured to transmit the beam from the laser, so that the beam impinges on the stone, and so that absorbed energy from the beam causes the stone to break. After insertion of the endoscope into the bladder, a beam from the laser is directed towards the stone, and the endoscope is configured to capture images of the stone, and of any fragments generated by the absorption of the laser beam, after the stone fractures. Typically the endoscope is configured to capture the images at a high frame rate, so that the fragments may be accurately tracked.

An image processor processes the captured images so as to identify, within a given captured image, images of fragments produced by the beam. The fragment images are typically identified and delineated using image processing techniques that compare an image of the stone prior to operation of the laser with an image after operation of the laser. The same type of identification and delineation may be applied to subsequent images captured by the endoscope. From the series of images the processor is able to construct tracks representing movements of the fragments, as well as a track illustrating movement of the remaining stone. The tracks may be displayed to an operator of the apparatus on a monitor coupled to the endoscope, the monitor also displaying a final image of the fragments and of any remaining stone, captured when there is no further movement of the fragments or stone.

Typically, for fragments that do not move beyond the field of view of the endoscope, a termination of the track of a given fragment shows a final location for the fragment. For fragments having a final location outside the field of view of the endoscope, so that there is no fragment image on the final image displayed on the monitor, a termination of the track may show, for example using an arrowhead, a direction indicative of a final location of the fragment.

DETAILED DESCRIPTION

Figure 1:
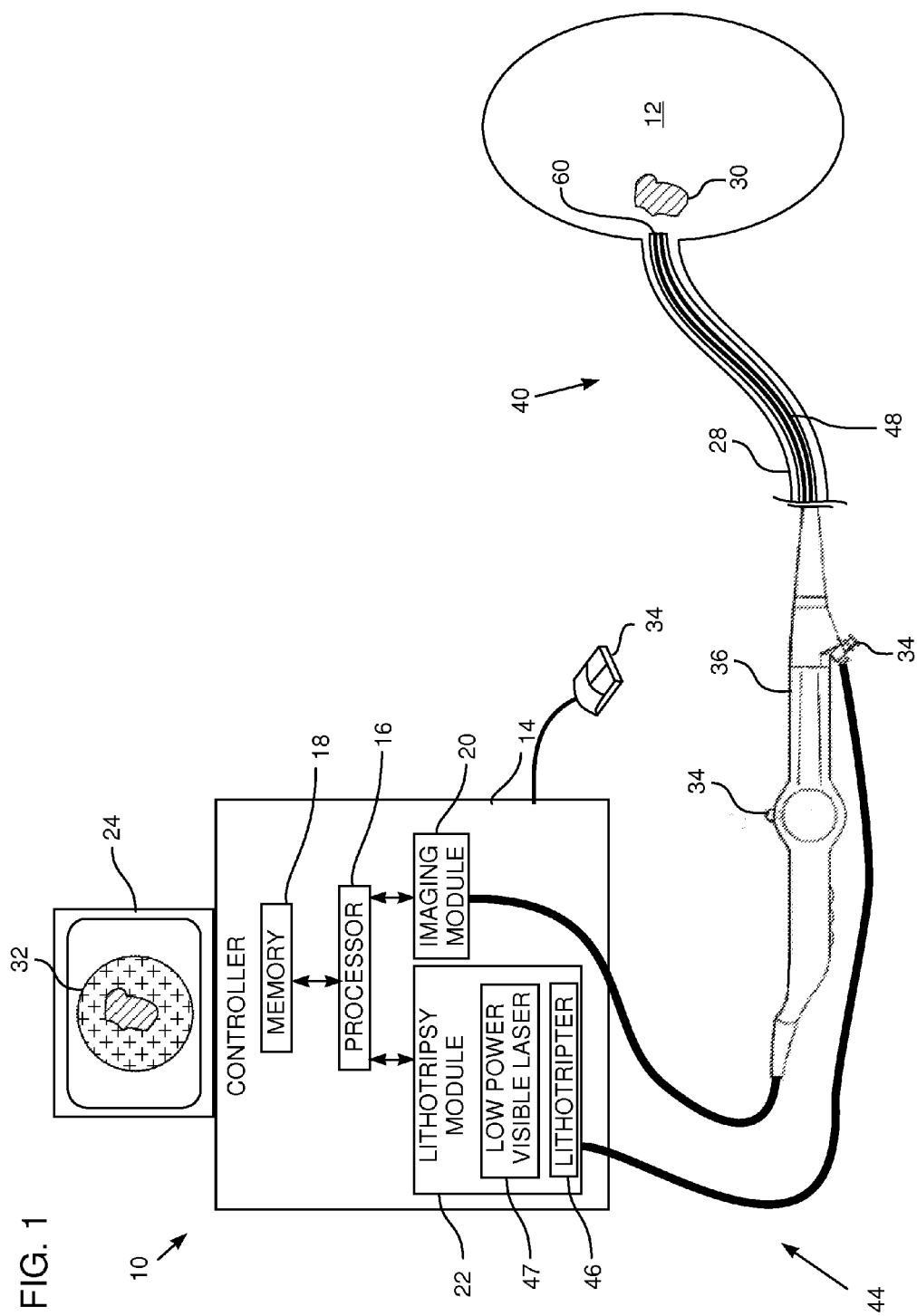
FIG. 1 is a schematic illustration of a lithotripsy system, according to an embodiment of the present invention.

Reference is now made to FIG. 1, which is a schematic illustration of a lithotripsy system 10, according to an embodiment of the present invention. System 10 may be used in an invasive medical procedure, typically a minimally invasive procedure, on a body lumen 12 of a human patient in order to remove stones or calculi in the body lumen. By way of example, in the present description, except where otherwise indicated, the body lumen is assumed to be the bladder of a patient, and body lumen 12 is also referred to herein as bladder 12. However, it will be understood that system 10 may be used to remove stones from substantially any human body lumen, such as the gastrointestinal organs, the bronchium, the chest, the salivary ducts, or from a non-human lumen.

System 10 is controlled by a controller 14, comprising a processor 16 which acts as an image processor and which communicates with a memory 18. Controller 14 also comprises an imaging module 20 and a lithotripsy module 22, whose functions are described below, and which may be implemented in software, hardware, or a combination of software and hardware. Controller 14 typically also comprises other modules, such as lumen illumination modules, which may be used by the processor in operating the imaging module; for simplicity these modules are not shown in the figure.

The processor uses software, typically stored in memory 18, to control system 10. Results of the actions performed by processor 16 may be presented on a monitor 24 to an operator, usually a medical physician, of system 10. The monitor typically displays to the operator images of a portion of body lumen 12 undergoing the procedure, or of an approach to the lumen, and/or a graphic user interface. The software for operating system 10 may be downloaded to processor 16 in electronic form, over a network, for example, or it may, alternatively or additionally, be provided and/or stored on non-transitory tangible media, such as magnetic, optical, or electronic memory.

To perform a procedure, an endoscope 26 may be passed to bladder 12 through a urethral tube 28. The procedure is assumed to comprise examination of a stone 30 in bladder 12, as well as fragmentation of the stone so as to remove the fragments from the bladder, or alternatively (if the fragmented particles are sufficiently small) to leave the fragments in the bladder. The operator of system 10 typically uses the endoscope to view the interior of bladder 12, so that controller 14 provides illumination for the endoscope and displays an image 32 of the stone, and/or of a portion of the bladder, acquired by the endoscope and using imaging module 20, on monitor 24. As described below, endoscope 26 acquires successive sequential images of the stone, and the images are presented in succession on monitor 24. In the present disclosure successive images 32 are differentiated from each other by having a letter appended to the identifying image numeral, so that there are successive images 32A, 32B, 32C, . . . . The successive images are generically referred to herein as images 32, and all images 32 are assumed to comprise the complete field of view of the endoscope. Details of the construction of endoscope 26 are provided below.

Interactive controls 34 enable the operator of system 10 to operate the controller. Controls 34 may comprise any convenient entities known in the art, coupled to controller 14, for operating a controller, such as a pointing device, a touch screen, a keypad and/or non-tactile entities such as voice control. By way of example, controls 34 are assumed to comprise a mouse, as is illustrated in the figure. Typically, in addition to the controls coupled to controller 14, at least some interactive controls 34 are assumed to be located in a handle 36 of the endoscope.

Lithotripsy system 10 comprises an imaging sub-system 40, which, using imaging module 20, acquires an image of objects in proximity to a distal end 60 of the endoscope. Elements in sub-system 40 are described below, with reference to FIG. 2.

Lithotripsy system 10 also comprises a lithotriptic subsystem 44, which uses a lithotripsic device 46, herein also termed lithotripter 46, incorporated in module 22. For simplicity, lithotripter 46 is herein, by way of example, assumed to comprise a high-power laser such as a Holmium:YAG laser transmitting at a wavelength of 2.1 μm, and is also referred to herein as laser 46. Lithotriptic sub-system 44 also comprises a low-power laser 47 transmitting radiation in the visible spectrum. Other elements of lithotriptic sub-system 44 are also described below. By way of example, elements of lithotripsic sub-system 44 are assumed to be introduced into lumen 12 using a working channel 48 of the endoscope.

Figure 2:
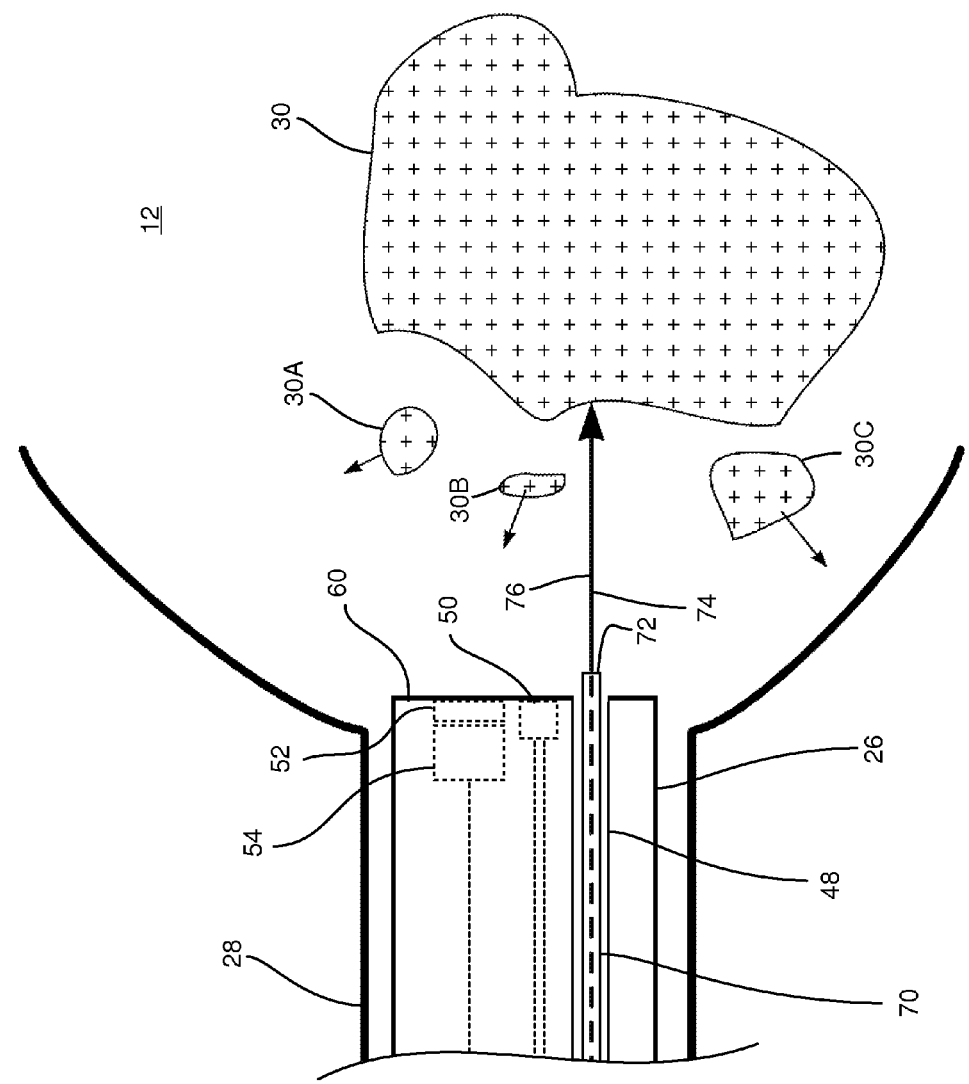
FIG. 2 is a schematic diagram illustrating a distal end of an endoscope, according to an embodiment of the present invention.

FIG. 2 is a schematic diagram illustrating distal end 60 of endoscope 26, according to an embodiment of the present invention. The distal end is assumed to be close to the entrance to bladder 12, having traversed urethral tube 28, and to be in proximity to stone 30. Imaging sub-system 40 comprises an illuminator 50, located at the distal end, which under control of imaging module 20 is able to radiate visible light. Returning light from an object illuminated by illuminator 50 is focused by a lens system 52 onto a semiconducting imaging array 54, which is also controlled by the imaging module, and which enables processor 16 to capture an image of the illuminated object.

Lithotriptic sub-system 44 comprises a fiber optic 70 that traverses working channel 48 and that is configured to be able to transmit from a fiber optic distal end 72 a high-power laser beam 74 generated by laser 46. Sub-system 44 is also configured to transmit a low-power visible wavelength laser beam 76, generated by low-power laser 47, from distal end 72 along substantially the same path as that taken by beam 74. Beams 74 and 76 are generated by, and are under control of lithotripsy module 22, and are described in more detail below.

Lithotriptic sub-system 44, when operative, is configured to break or fracture stone 30. While typically the breaking may produce many fragments of the stone, for clarity in the following description the breaking of the stone is assumed to generate three stone fragments 30A, 30B, and 30C.

Figure 3:
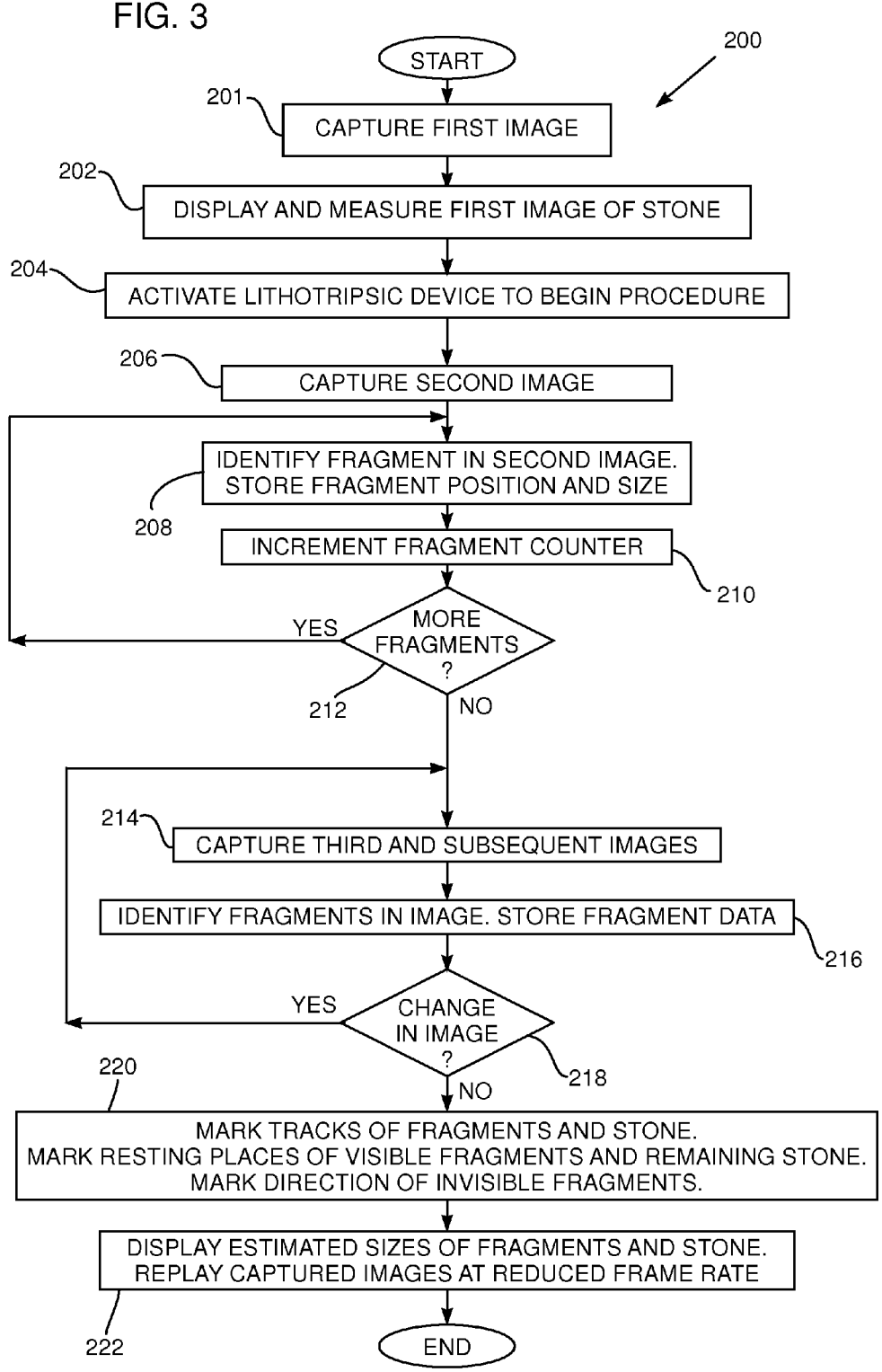
FIG. 3 is a flowchart of steps performed by a processor in operating the system of FIG. 1, according to an embodiment of the present invention.

FIG. 3 is a flowchart 200 of steps performed by processor in operating system 10, and FIGS. 4-13 are schematic diagrams of images presented on monitor 24, illustrating the steps, according to embodiments of the present invention. The steps of the flowchart are described assuming that stone 30 is to be removed from bladder 12. For clarity and simplicity, the following description of the steps assumes that once inserted into the bladder, a direction of view of endoscope 26 does not change during implementation of the steps. Such is typically the case for manual insertion of the endoscope by an operator of system 10. However, in some embodiments the direction of view of the endoscope may be controlled robotically, so that the direction of view may be changed automatically, under overall control of processor 16. An example of such an automated change of direction of view of the endoscope is provided below.

Figure 4:
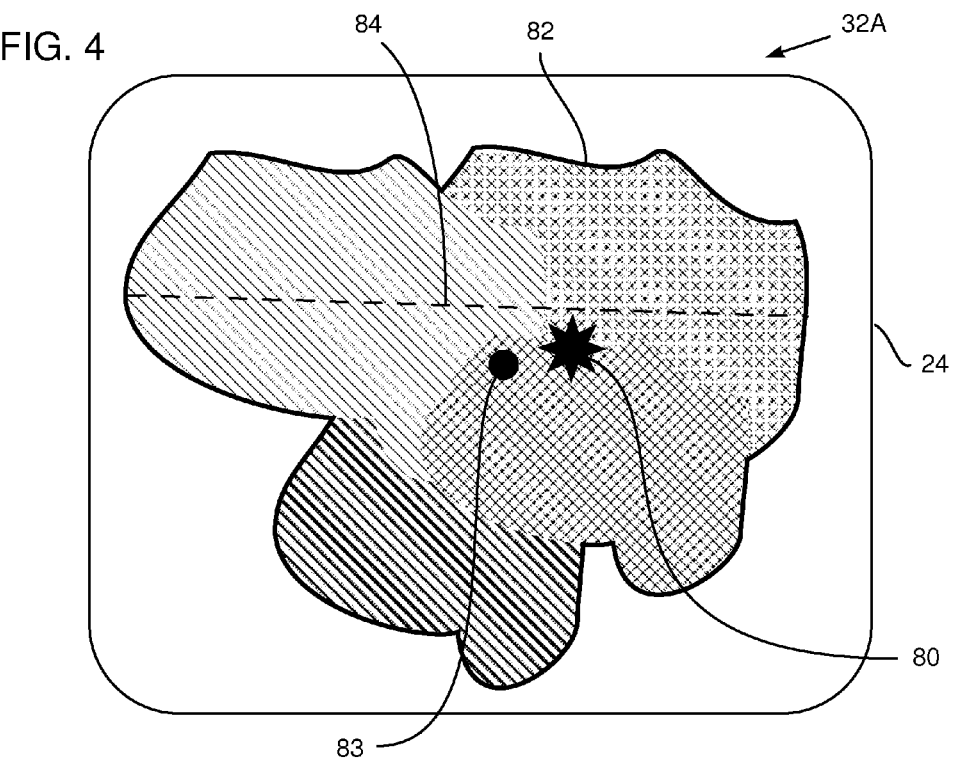

In an initial step 201, the operator of the system inserts endoscope 26 into bladder 12, as illustrated in FIGS. 1 and 2. An image of the scene captured by the endoscope is generated by imaging module 20, using illuminator 50 and array 54. The image is presented to the operator on monitor 24, and the operator maneuvers the endoscope to generate a desired image of stone 30 on the monitor. Typically, once the desired image of the stone has been realized by the operator and captured, he/she activates low-power laser 47 to transmit beam 76 so as to illuminate a section of the stone that is to be irradiated by lithotripter 46. FIG. 4 is a schematic diagram of a first image 32A presented to the operator on monitor 24, illustrating the desired stone image and within the image a region 80 corresponding to the laser-illuminated section of the stone. The operator typically uses controls 34 so that processor 16 captures and stores image 32A, typically while region 80 may be illuminated by illuminator 50.

In a display step 202, processor 16 displays the image, and uses the image to measures and store parameters indicative of a size and a location of the stone. The processor is typically configured to automatically calculate the parameters, such as by delineating an outer bound 82 of the stone, and finding a centroid 83 of the bound and the length of a largest line segment 84 traversing the bound.

In a lithotripsy step 204, the system operator uses controls 34 to activate device 46, so as to irradiate stone 30 with high-power laser beam 74 in order to break the stone. Beam 74 is typically pulsed, and the system operator may adjust parameters of the pulses, such as their width, frequency, and power, prior to activating device 46. Step 204 initiates a fragmentation procedure for the stone.

Processor 16 is configured to control the frame rate at which images are captured by endoscope 26, and images generated during the fragmentation procedure are typically captured at a higher frame rate than is used to display images of stone 30 when it is not being fragmented. For example, procedure images may be captured at a rate of 300 frames/second, while a typical capture rate for stone 30 when it is being viewed while not undergoing the fragmentation procedure may be 30 frames/second. Typically, while the higher frame rate is being used, illuminator 50 increases the illumination intensity it provides so as to maintain a signal-noise level of the captured image at an acceptable level.

Figure 5:
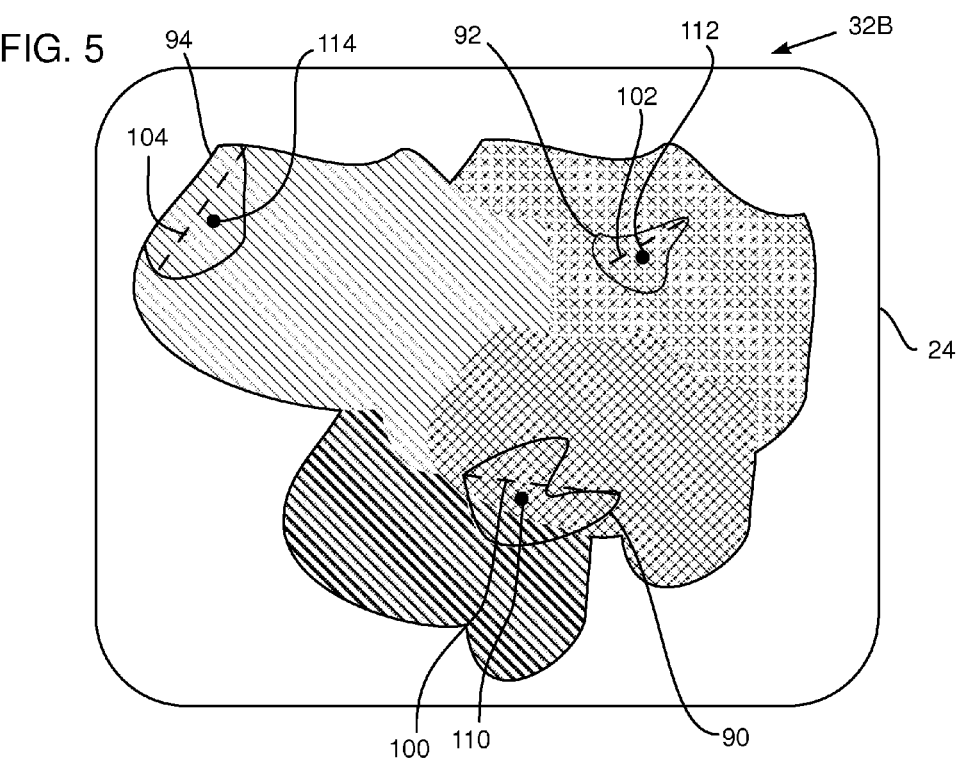

In an imaging step 206, typically implemented simultaneously with lithotripsy step 204, processor 16 captures and stores a second image 32B of stone 30 after its fragmentation by beam 74. FIG. 5 is a diagram of image 32B, schematically illustrating images 90, 92, 94 of fragments 30A, 30B, 30C (FIG. 2) of the stone created by beam 74.

In a fragment identification step 208, the processor compares image 32B with image 32A in order to identify and delineate a given fragment image. In performing the comparison, the processor typically uses pattern recognition methods, well known in the art, in order to identify a contiguous region having bounds present in image 32B and not present in image 32A. Once a fragment has been delineated, the processor stores a location for the fragment, typically as a centroid of the fragment image. In addition, the processor measures and stores a parameter indicative of a size of the fragment, typically using substantially the same method as used in step 204.

As indicated in the flowchart and as described further below, step 208 is reiterated, and at each iteration, in a counting step 210, the processor increments a counter giving the number of fragments identified in step 208, i.e., in step 210 the processor evaluates a cardinality of the fragments.

The iterations of step 208 continue while a comparison step 212, checking if the processor can identify further fragments, returns a positive value. When the processor determines that there are no further fragments, comparison step 212 returns a negative value, and the flowchart continues to a subsequent procedure imaging step 214.

Image 32B illustrates, by way of example, that in the reiteration of step 208 the processor identifies three fragment images 90, 92, and 94, respectively corresponding to fragments 30A, 30B, and 30C. For each fragment image the processor generates line segments 100, 102, and 104, measures the length of the segments, and uses the lengths as respective parameters indicative of the size of the fragments.

The processor also determines centroids 110, 112, 114 for each of the fragment images, and uses the centroids as parameters indicative of the location of the fragments.

In subsequent procedure imaging step 214 the processor captures and stores third and subsequent procedure images of stone 30 and its fragments. Thus, a third image 32C is captured after image 32B has been acquired. FIG. 6 is a diagram of image 32C, schematically illustrating by way of example images 120, 122, and 124 of the three fragments 30A, 30B, and 30C of the stone originally identified in image 32B.

In a fragment tracking step 216, the processor compares image 32C with image 32B in order to identify, and to locate and delineate, each of the fragments identified in step 208. The comparison typically uses similar pattern recognition methods to those used in step 208, and typically also comprises applying preset translation limits to the possible new location of any given fragment compared to the previous location of the fragment. In addition, any given fragment imaged in image 32C may have rotated from its orientation when imaged in image 32B, and so present a different aspect to endoscope 26 from the aspect captured in image 32B. The processor may accommodate such changes in aspect by applying preset bounding limits to possible changes in delineation of the bounds of the fragment. The system operator may determine values for the translation and bounding limits without undue experimentation prior to operation of system 10, typically, for example, by analysis of images generated in previous lithotripsy procedures.

In step 216, for each identified fragment, the processor calculates and stores a parameter indicative of a location of the fragment, as well as a parameter indicative of the size of the fragment, typically using substantially the same method as used in step 208.

Image 32C illustrates that in step 216 the processor identifies the three fragments 30A, 30B, and 30C, initially identified in image 32B, as respectively having images 120, 122, and 124. For each image the processor generates line segments 130, 132, and 134 and uses the lengths of the segments as respective parameters indicative of the size of the fragments. The processor also calculates centroids 140, 142, and 144, and uses these as indicative of the fragment location.

It will be understood that the values of the parameters indicating the size of the fragments, herein by way of example assumed to be the length of the longest line segment of the image of the fragment, may change from image to image. The change may typically be caused by factors which will be apparent to those having ordinary skill in the art, such as rotation of the fragment, and/or change of the distance of the fragment from the distal end of the endoscope.

Processor 16 reiterates steps 214 and 216, capturing and analyzing successive images acquired by endoscope 26. As each specific image is captured, the processor, in a comparison step 218, compares the image with the preceding image. If there is a change in the images, indicating that at least one of the fragments identified in the images is moving, the comparison returns a positive value so that the reiteration continues.

Figure 8:
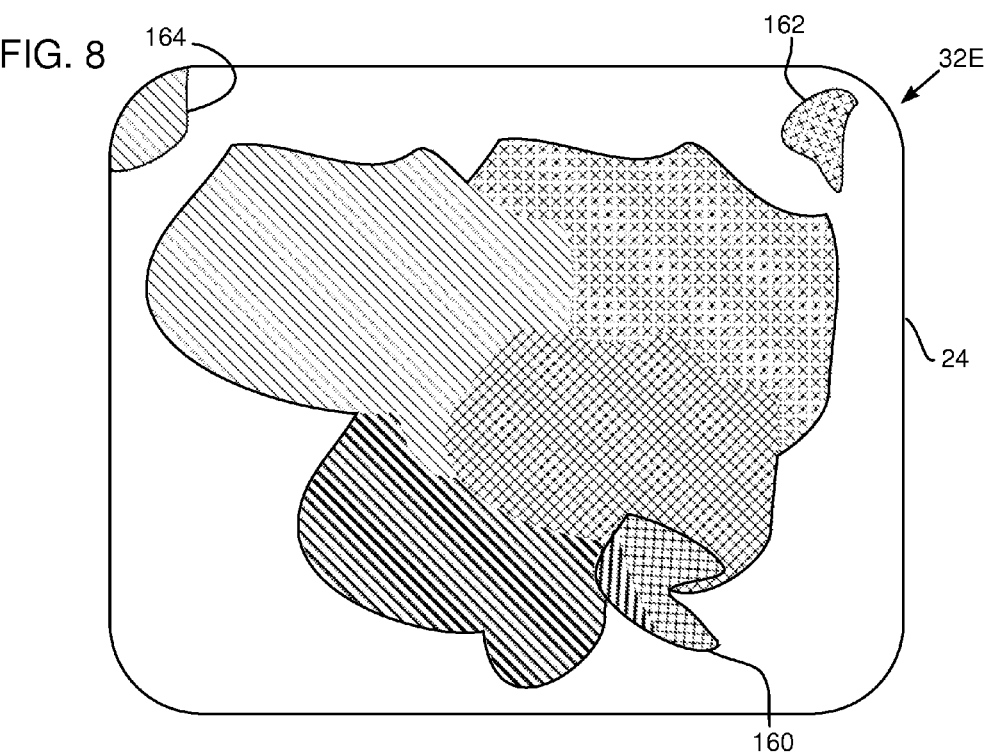
Figure 9:
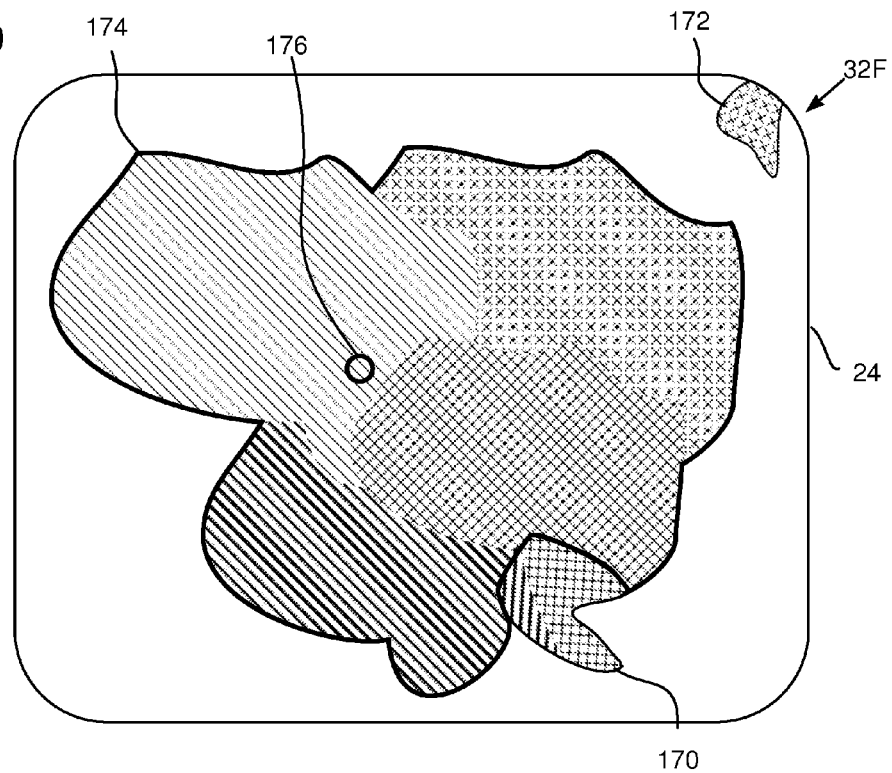
Figure 10:
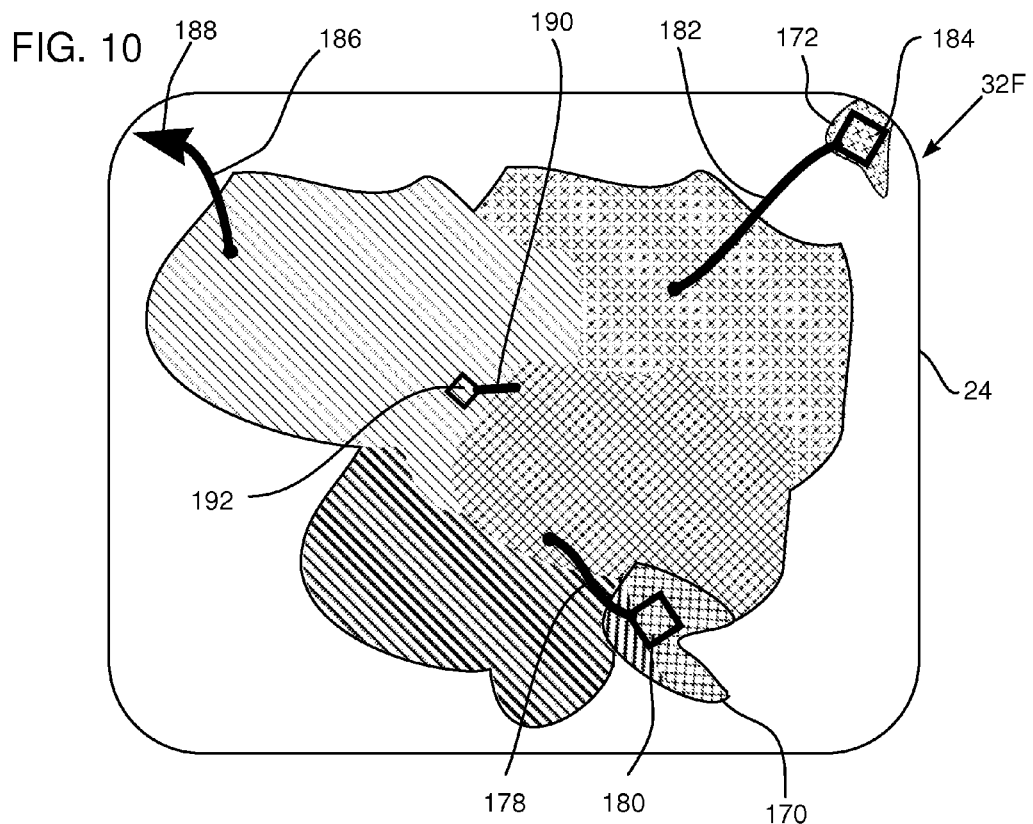

FIGS. 7, 8, and 9 schematically illustrate typical successive images 32D, 32E, and 32F that processor 16 may capture during the reiteration of steps 214 and 216. While images 32C, 32D, 32E, and 32F are captured at succeeding progressively later times, it will be appreciated that the images are typically not consecutive, so that the processor may capture intervening images between images 32C and 32D, as well as intervening images between images 32D and 32E and between images 32E and 32F.

In FIG. 7, the processor identifies images 150, 152, and 154 as respectively corresponding to fragments 30A, 30B, and 30C of stone 30. It will be appreciated that in FIG. 7 images 150, 152, and 154 are complete images of fragments 30A, 30B, and 30C, due to the fragments being completely in the field of view of the endoscope. In FIG. 8, the processor identifies images 160, 162, and 164 as respectively corresponding to fragments 30A, 30B, and 30C of stone 30. Images 160 and 162 are complete images of fragments 30A and 30B, since the fragments are completely in the field of view of the endoscope. However image 164 is only a partial image of fragment 30C, corresponding to the fragment being only partially in the endoscope's field of view.

Processor 16 generates indications of the locations and sizes of the fragments from the images in FIGS. 7 and 8, including partial image 164, typically as described above for the fragment images illustrated in FIGS. 5 and 6, i.e. by calculating centroids and longest line segments for the fragment images. However, for simplicity the centroids and line segments are not shown in FIGS. 7 and 8, or in FIG. 9 (described below).

FIG. 9 schematically illustrates a "final" image 32F that processor 16 captures. Image 32F is assumed to be acquired as the last image of the reiteration of steps 214 and 216, i.e., when the comparison of step 218 returns a negative value. In image 32F the processor identifies image 170 and image 172 as corresponding respectively to fragments 30A and 30B. Image 170 is a complete image of fragment 30A since the fragment is completely in the field of view of the endoscope, image 172 is a partial image of fragment 30B since the fragment is partially in the field of view, and there is no image for fragment 30C because the fragment is outside the endoscope field of view.

Returning to the flowchart, once step 218 returns a negative value, the fragmentation procedure initiated in step 204 is assumed to have terminated, and the processor continues to a graphic display step 220. In step 220 the processor uses image 32F to calculate and store a parameter indicative of a location of the stone remaining after the fragmentation procedure, i.e., of stone 30 absent all identified fragments. The processor is typically configured to automatically calculate the parameter, by delineating an outer bound 174 of the remaining visible stone, and finding a centroid 176 of the bound. Outer bound 174 is assumed to be delineated in image 32F while excluding any images of fragments; thus, the outer bound does not include image 170.

Using the locations calculated in steps 208 and 216, processor 16 is able to display, typically by the system operator using controls 34, tracks of movements of fragments generated during the procedure as well as final locations of fragments or parts of fragments that are visible in image 32F. Thus in image 32F the processor is able to display a track 178 and a final location 180 for fragment 30A, and a track 182 and a final location 184 for fragment 30B. In the figures, final locations are indicated by a square. For fragments that were identified in step 208, but which are no longer visible in image 32F, i.e., which are no longer in the field of view of the endoscope, the processor is able to use the step 208 and step 216 locations to display a track of the fragment's movement together with an arrowhead indicating a direction in which the fragment moved on exiting the endoscope field of view. Thus in image 32F the processor is able to display a track 186 and a directional arrowhead 188 for fragment 30C.

In addition to displaying tracks and final location information for the fragments from stone 30, the processor is able to use the locations stored in steps 202 and 220 to display a track for the movement of the remaining stone, as well as the remaining stone's final location. Thus in image 32F the processor is able to display a track 190 and a final location 192 for the remaining stone.

In a final step 222, the processor analyzes the size parameters for each fragment that have been stored in steps 208 and 216. Typically for any given fragment the size parameters vary from image to image, as the fragment moves and/or rotates in the field of view of the endoscope. From the size parameters the processor estimates a largest linear measurement for each fragment. In addition, using the size parameter for stone 30 stored in step 202, the processor estimates a largest linear dimension for the stone, and may also estimate ratios of the estimated fragment dimensions to the estimated stone dimension.

In addition, the size dimensions of any given fragment enable the processor to estimate a volume of the fragment, by methods which are known in the art, such as by computing a mean value of a function of a cube of the size parameter. A similar estimation may be made for a volume of stone 30, using the size parameter of step 202. The processor may use the volume estimates to generate a ratio of the total fragment volume to the volume of stone 30.

The operator may use controls 34 to display the estimated data of the fragments and the stone derived by the processor, and as described above, on monitor 24. From the counter value generated in step 206, the processor is also able to display on monitor 24 a number of fragments generated by the fragmentation procedure.

As stated above, the images that the processor stores are acquired at a high frame rate. In final step 222 the operator may replay the images of the fragmentation procedure at a lower frame rate, in order, for example, to more clearly see characteristics of the fragments generated by the procedure. Additionally, the operator may reiterate all the steps of the flowchart, for example by applying a "clear screen" function, and returning the system to first step 201.

It will be understood that the description of flowchart 200 assumes that processor 16 is able to capture and analyze images "on the fly." In such a case, it will also be understood that in the case of an endoscope having a direction of view that is robotically controlled, under overall control of processor 16, the processor may change the direction of view during the fragmentation procedure described above. For example, the processor may be implemented to use the location of a particular fragment, such as the largest fragment, as determined from the captured images of steps 206 and 214, so as to change the direction of view of the endoscope in order to track the particular fragment.

The above description describes a scenario where the fragmentation procedure initiated in step 204 and terminating in step 218 results in fragments of stone 30 having images that may typically overlay an image of the remaining stone. Such a scenario may occur if the fragments are relatively small in comparison to the stone.

Figure 11:
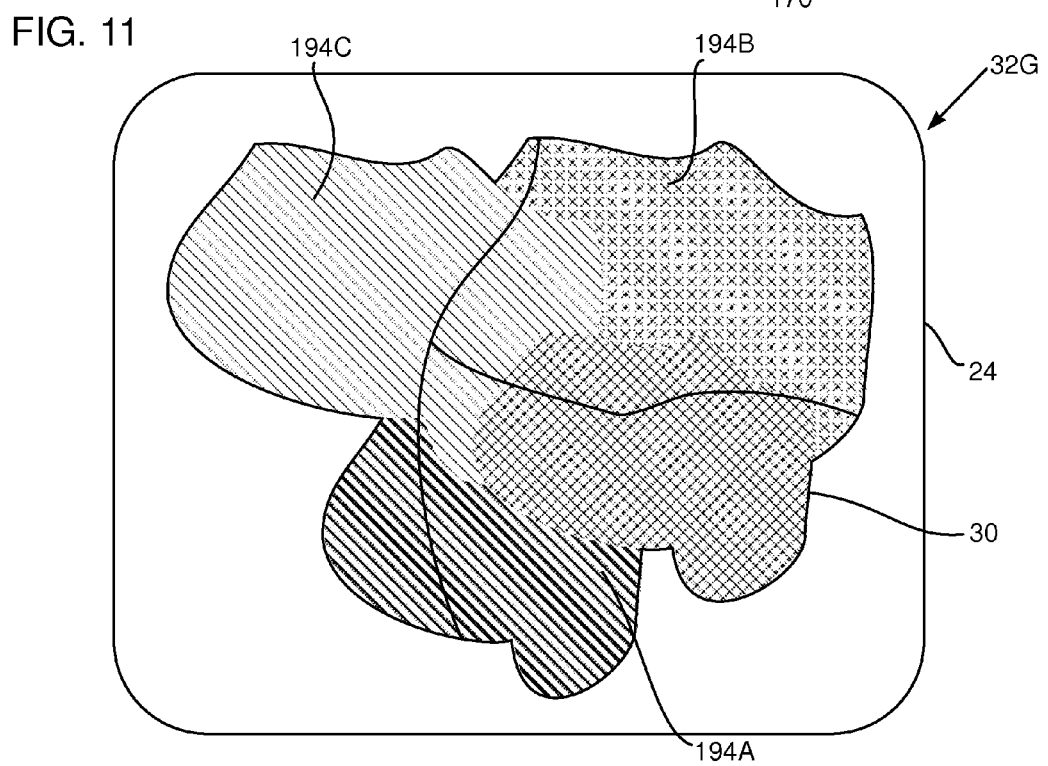

FIGS. 11, 12, and 13 schematically illustrate an alternative scenario resulting from the fragmentation procedure, wherein the fragments of stone 30 have a size that is relatively large, typically being of the same order as the stone size.

In the alternative scenario the fragmentation procedure initiating in step 204 is assumed to break stone 30 into three large fragments, herein referred to as the first, second, and third fragments. In this case an initial image 32G (FIG. 11) of the three fragments, captured in step 206, i.e., at the beginning of the fragmentation procedure, shows respective fragment images 194A, 194B, and 194C of the first, second, and third fragments.

A subsequent intermediate image 32H (FIG. 12) of the three fragments, captured in step 214 while the step is reiterating, shows fragment images 195A, 195B, and 195C. Image 195A is only partial, since the first fragment is only partially in the field of view of the endoscope. Images 195B and 195C are complete since the second and third fragments are completely in the field of view.

A final image 32I (FIG. 13), captured in step 214 when the step no longer reiterates, i.e., when comparison 218 returns a negative value, shows fragment images 196B and 196C. In the final image there are only two fragment images, since the first fragment is no longer in the endoscope field of view. In image 32I image 196C is partial corresponding to the third fragment being only partially in the endoscope field of view.

It will be understood that the operations described above for flowchart 200 may be applied, mutatis mutandis, to the alternative scenario illustrated in FIGS. 11-13. For example, as shown in FIG. 13, the processor may display tracks 197A, 197B, and 197C of the first, second, and third fragments, together with a final location of the fragment or an arrowhead indicating a direction of the fragment when it is outside the field of view of the endoscope. Other actions described above for steps 220 and 222 and applicable to other scenarios, such as the alternative scenario described above, will be apparent to those having ordinary skill in the art, and for brevity will not be described here.

FIG. 14 is a flowchart 300 of steps performed by processor 16 in operating system 10, according to an alternative embodiment of the present invention. The process of flowchart 300 comprises substantially the same steps as those of flowchart 200, and the actions of the steps are as described above with respect to flowchart 200. However, in contrast to flowchart 200, processor 16 may not operate "on the fly." Rather, in flowchart 300 imaging steps 206 and 214 are implemented sequentially, so that all images from the fragmentation procedure are available to the processor prior to any analysis in later steps 208, 210, 212, . . . .

From consideration of the scenarios illustrated in FIGS. 4-13 it will be understood that the process described for flowcharts 200 and 300 may be applied to substantially any type of fragmentation produced by the fragmentation procedure referred to above, i.e., where a stone is broken by a lithotripsic device, and where the fragments produced by activation of the device are tracked and tracks of the fragments are presented to an operator of the device.

Returning to the description of step 201 (FIG. 3 and FIG. 14), it will be understood that it is not necessary for the operator to initiate capture of first image 32A. For example, once the endoscope is inserted into bladder 12, it may be configured to capture images. The processes of flowcharts 200 or 300 may be begun, mutatis mutandis, once a stone has been identified in a captured image, and such identification may be set up automatically. Alternatively, the captured images may be stored in a memory buffer, and initial image 32A may be selected as the last stored image before activation, in step 204, of the lithotripsic device.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A medical apparatus, comprising:
   a lithotripsic device comprising a laser configured to break a stone into one or more fragments in a body lumen;
   an endoscope configured to obtain a captured image in the body lumen; and
   an image processor configured:
      to process the captured image and create a processed image for display on a monitor, and
      to process and display a track of a movement of at least one of the stone or the one or more fragments.

2. The apparatus according to claim 1, wherein the processed image comprises an image of a final location of the at least one of the stone or the one or more fragments, and wherein the image processor is configured to provide an indication of the final location on the processed image.

3. The apparatus according to claim 1, such that when a final location of the at least one of the stone or the one or more fragments is outside a field of view of the endoscope, the image processor is configured to provide an indication of a direction of the final location.

4. The apparatus according to claim 1, wherein the image processor is configured to measure a dimension of the stone, and a corresponding dimension of the one or more fragments, and to provide a comparison of the corresponding dimension to the dimension.

5. The apparatus according to claim 1, wherein the image processor is configured to evaluate a cardinality of the fragments.

6. The apparatus according to claim 1, wherein the image processor is configured to provide a comparison of a total size of the fragments to a size of the stone.

7. The apparatus according to claim 1, wherein the image processor is configured to control a frame rate at which the endoscope obtains the captured image, and to increase the frame rate at least during activation of the lithotripsic device.

8. The apparatus according to claim 7, wherein the image processor is configured to display the captured image at a lower frame rate than the increased frame rate on the monitor.

9. The apparatus according to claim 1, wherein a direction of view of the endoscope is controlled by the image processor, and wherein the image processor is configured to determine a location of one of the one or more fragments from the captured image, and to change the direction of view of the endoscope in response to the location so as to track the one of the one or more fragments.

* * * * *